United States Patent
Nawy et al.

(10) Patent No.: US 9,348,971 B2
(45) Date of Patent: May 24, 2016

(54) TWO WAY SHORT MESSAGE SERVICE (SMS)-ENABLED BLOOD GLUCOSE METER AND RELATED COMMUNICATIONS SYSTEMS AND METHODS

(71) Applicant: ERP Systems Corp., Eatontown, NJ (US)

(72) Inventors: Robert Nawy, Lincroft, NJ (US); Daniel W. Havens, San Diego, CA (US); Richard Jacques Fortier, San Diego, CA (US)

(73) Assignee: ERP SYSTEMS CORP., Eatontown, NJ (US)

( * ) Notice: Subject to any disclaimer, the term of this patent is extended or adjusted under 35 U.S.C. 154(b) by 251 days.

(21) Appl. No.: 13/661,445

(22) Filed: Oct. 26, 2012

(65) Prior Publication Data

US 2013/0109417 A1 May 2, 2013

Related U.S. Application Data

(60) Provisional application No. 61/551,572, filed on Oct. 26, 2011.

(51) Int. Cl.
| | |
|---|---|
| *H04W 4/00* | (2009.01) |
| *G06F 19/00* | (2011.01) |
| *G08B 1/08* | (2006.01) |
| *A61B 5/145* | (2006.01) |
| *H04W 4/14* | (2009.01) |
| *H04L 12/58* | (2006.01) |
| *H04L 29/08* | (2006.01) |

(52) U.S. Cl.
CPC ......... *G06F 19/3418* (2013.01); *A61B 5/14532* (2013.01); *H04L 51/38* (2013.01); *H04L 67/12* (2013.01); *H04W 4/14* (2013.01)

(58) Field of Classification Search
CPC ......................................................... G08B 1/08
USPC ..................................................... 340/539.12
See application file for complete search history.

(56) References Cited

U.S. PATENT DOCUMENTS

| | | | | |
|---|---|---|---|---|
| 6,992,580 | B2 * | 1/2006 | Kotzin et al. | 340/539.11 |
| 7,894,849 | B2 * | 2/2011 | Kass et al. | 455/550.1 |
| 2007/0168224 | A1 | 7/2007 | Letzt et al. | |
| 2008/0119705 | A1 * | 5/2008 | Patel et al. | 600/347 |
| 2008/0139910 | A1 | 6/2008 | Mastrototaro et al. | |

(Continued)

OTHER PUBLICATIONS

International Search Report and Written Opinion of the International Searching Authority for International Patent Application No. PCT/US 12/62083 mailed Jan. 9, 2013.
Benjet. "GlucoPhone—Glucometer and Cell Phone in One!" [online] published May 3, 2007. [retrieved on Dec. 20, 2012] Retrieved from the Internet<URL: http://www.healthcentral.com/diabetes/c/117/9164/cell-phone>p. 4, 5, and 6.

*Primary Examiner* — Huy C Ho
(74) *Attorney, Agent, or Firm* — Lowenstein Sandler LLP

(57) ABSTRACT

A system and method for two way short message service (SMS)-enabled BGM and related communications is presented. The method includes receiving, by a processing device integrated with a blood glucose meter (BGM), a first short message service (SMS) message comprising a question, presenting the question at the BGM, receiving a response to the question, translating the response to the question into a second SMS message, translating blood glucose measurement information into a third SMS message, the blood glucose measurement information received from a test of a user by the BGM, and transmitting the second and third SMS messages to a receiver.

20 Claims, 6 Drawing Sheets

(56) References Cited

U.S. PATENT DOCUMENTS

| | | | |
|---|---|---|---|
| 2009/0088607 A1 * | 4/2009 | Muraca | 600/300 |
| 2009/0240120 A1 | 9/2009 | Mensinger et al. | |
| 2010/0240979 A1 | 9/2010 | Atkin | |
| 2010/0279418 A1 | 11/2010 | Larson et al. | |

* cited by examiner

TWO WAY SHORT MESSAGE SERVICE (SMS)-ENABLED BLOOD GLUCOSE METER AND RELATED COMMUNICATIONS SYSTEMS AND METHODS

CROSS-REFERENCE TO RELATED APPLICATIONS

The present application claims the benefit, pursuant to the provisions of 35 U.S.C. 119, of U.S. Provisional Application Ser. No. 61/551,572, titled "Two Way SMS-Enabled Blood Glucose Meter and Related Communications Systems and Methods", filed on Oct. 26, 2011, which is herein incorporated by reference.

FIELD OF THE INVENTION

The present invention relates generally to a system and a method for communications involving a blood glucose meter (BGM), more particularly to a system and method for two way short message service (SMS)-enabled BGM and related communications.

BACKGROUND OF THE INVENTION

A blood glucose meter (BGM) or glucometer is a medical device for determining the approximate concentration of glucose in the blood. It is a key element of home blood glucose monitoring by people with, e.g., diabetes mellitus or hypoglycemia. A small drop of blood, obtained by pricking the skin with a sterile lancet, is placed on a disposable test strip that the BGM reads and uses to calculate the blood glucose level.

The value of frequent monitoring of blood glucose as a means to avoid or mitigate the complications of certain diseases such as diabetes mellitus or hypoglycemia is well established. However, many people monitor their blood glucose levels infrequently or incorrectly, which may result in a catastrophic condition that requires ambulatory services and a visit to a hospital emergency room. Therefore, the ability to accurately and conveniently monitor blood glucose levels and transmit the data to a database is important.

BRIEF DESCRIPTION OF THE DRAWINGS

The present invention will be more readily understood from the detailed description of embodiments presented below considered in conjunction with the attached drawings, of which.

It is to be understood that the attached drawings are for purposes of illustrating the concepts of the invention.

DETAILED DESCRIPTION OF THE INVENTION

Embodiments of the present invention are directed to a system and method for a two-way short message services (SMS)-enabled BGM and related communications.

In one embodiment, the system of embodiments of the disclosure includes a BGM configured to receive, by a receiver and a processing device integrated with the BGM, a first short message service (SMS) message from a medical provider. The first SMS message may comprise a medically related question for a user. The BGM may present the question to the user and receive a response to the question from the user. The BGM may translate the response to the question into a second SMS message, translate blood glucose measurement information received from a test of the user into a third SMS message, and transmit the second and third SMS messages to a central data center. In some embodiments, the central data center may then translate the SMS message and extract relevant data associated with the BGM for transmission to a medical provider associated with the BGM.

In the following description, numerous details are set forth. It will be apparent, however, to one skilled in the art, that the present invention may be practiced without these specific details. In some instances, well-known structures and devices are shown in block diagram form, rather than in detail, in order to avoid obscuring the present invention.

Figure 1:
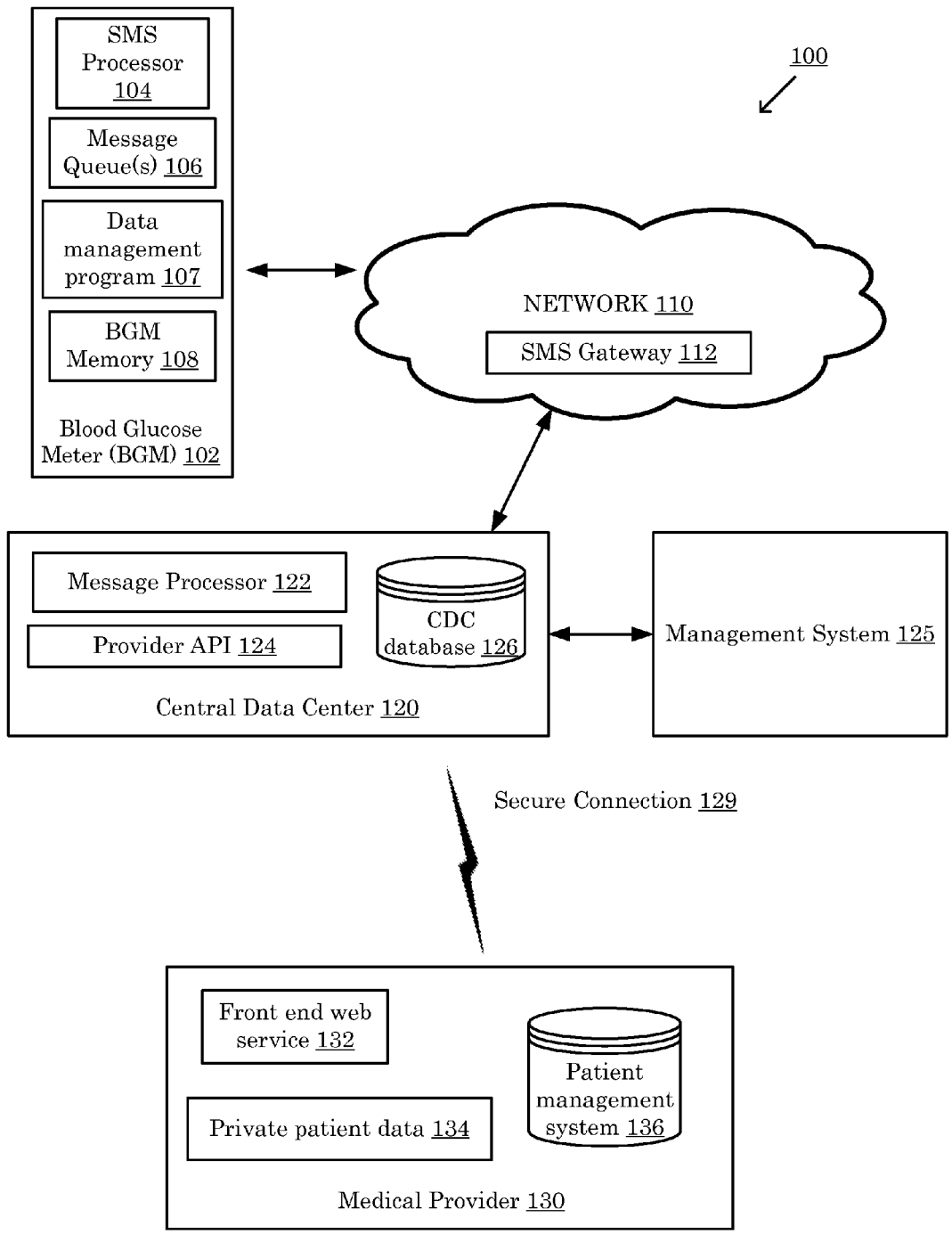
FIG. 1 is a block diagram of a system for two way short message services (SMS) enabled BGM and related communications in accordance with embodiments of the present invention.

FIG. 1 illustrates a block diagram of a networked environment 100 including a blood glucose meter (BGM) 102, according to embodiments of the present invention. The BGM 102 is a medical device for determining the approximate concentration of glucose in the blood. In an embodiment, the BGM 102 may include a short message service (SMS) processor 104. SMS is a text messaging service component of phone, web, or mobile communication systems, using standardized communications protocols that allow the exchange of short text messages between fixed line or mobile phone devices. In an embodiment, the SMS processor 104 may process and facilitate sending, receiving, playing, and displaying SMS messages at the BGM 102. As used herein, the term "processor" or a "processing device" is intended to include, but is not limited to, a programmable electronic machine that performs executes software to perform several operations such as assemble, store, correlate, or otherwise processes information.

In an embodiment, the BGM 102 may include one or more message queues 106. The message queue(s) 106 may include one or more queues used to store SMS messages received at the BGM 102 and/or SMS messages to be sent from the BGM 102. In some embodiments, the message queue(s) 106 may interact with BGM memory 108 to provide storage of the SMS messages tracked by message queue(s) 106. The message queue(s) 106 may store SMS messages that have been received from an external source and are to be presented to a user of the BGM 102. The message queue(s) 106 may also store SMS messages generated at the BGM 102 that are to be sent to the external source.

In an embodiment, the BGM 102 also includes a data management program 107. The data management program 107 may be a computer software program configured to take blood glucose reading tests to calculate blood glucose levels of a user of the BGM 102. The data management program 107 may maintain the blood test data and other associated data used for administering such tests.

The networked environment 100 may include a network 110 (e.g., the Internet, or the wired or wireless telephone network), which may be any type of communications medium that allows for the SMS messages to be communicated between the BGM 102 and an SMS gateway 112, as shown in FIG. 1. In one embodiment, the SMS gateway 112 is a telecommunications network facility for sending or receiving SMS transmissions to or from a telecommunications network that support SMS. The SMS gateway 112 may be a network node that is equipped and configured for interfacing with another network that may use a different communications protocol. In some embodiments, the SMS gateway 112 may be managed by a third-party provider, such as a mobile network operator.

In one embodiment, the BGM 102 is configured to communicatively connect to the SMS gateway 112 via the network 110. The BGM 102 may include, but is not limited to, any transmitter and/or receiver that are capable of communicating with the SMS gateway 112 via the network 110. In an embodiment, the BGM 102 communicates with the network 110 via a wireless connection using network protocols such as, but not limited to, code division multiple access (CDMA) and global system for mobile (GSM).

The networked environment 100 may also include a central data center (CDC) 120. In an embodiment, the CDC 120 may be a server or any other computing device that runs one or more services associated with the BGM 102. Examples of services include, but are not limited to, interfacing with the SMS gateway 112 to send and receive SMS messages associated with the BGM 102, processing SMS messages associated with the BGM 102, providing access to BGM 102 data, provisioning new BGMs 102, providing message requests to the BGM 102, and providing administrative functions associated with the BGM 102 to a medical provider 130 associated with the BGM 102. As shown in FIG. 1, the CDC 120 includes, but is not limited to, a message processor 122, a provider API 124, and a CDC database 126. Further details related to services provided by the CDC 120 are discussed below with respect to FIGS. 2 through 5.

In an embodiment, the message processor 122 may process and facilitate transmitting and receiving SMS messages to and from the BGM 102 via the SMS gateway 112 and the network 110. The message processor 122 may execute one or more computer software programs configured to perform the functions described in detail below.

In an embodiment, the provider API 124 is an application or a module configured to enable an administrator of the BGM 102 (e.g., such as medical provider 130) to obtain access to data of existing BGMs 102 and to provision new BGMs 102 for distribution to a patient or user. In addition, the provider API 124 facilitates the processing of inbound and outbound SMS messages to the BGM 102. The provider API 124 may include any computer program including one or more sets of instructions provided to implement the methods as described below. In one embodiment, the provider API 124 provides a graphical user interface (GUI) for display at a computing device of the administrator of the BGM 102 to enable the administrator to interface with the provider API 124.

In an embodiment, the CDC database 126 stores a plurality of SMS messages that are accessed and used by the message processor 122 and provider API 124. As used herein, the term "database" is intended to include, but is not limited to, a repository for containing and storing data. The CDC database 126 may be a non-transitory computer-readable storage medium (e.g., a hard drive). In another embodiment, the provider API 124 resides on the computer-readable storage medium (e.g., a hard drive) 126.

In one embodiment, the CDC 120 is communicatively connected to a management system 125. Management system 125 may be part of central data center 120 or may be provided by a separate computing device, such as a server device, than the central data center 120. The management system 125 may monitor status of each of the SMS gateway 112, CDC database 126, message processor 122, provider API 124, and/or any hardware used to implement the networked environment 100.

The CDC 120 is configured to communicatively connect to the SMS gateway 112 via the network 110. The CDC 120 may include any transmitter and receiver components that are capable of communicating with the SMS gateway 112 via the network 110. In an embodiment, the CDC 120 communicates with the network 110 via a wireless connection using network protocols and a communications protocol module such as, for example, a communications protocol module for code division multiple access (CDMA) and for global system for mobile (GSM).

In one embodiment, the CDC 120 is also configured to communicatively connect to a medical provider 130 via a secure connection 129. The secure connection 129 may be, but is not limited to, an internet connections made secure by provision of firewall security to prevent hackers, snoopers or spam-mail senders, or via encryption of messages, typically used for a virtual private network (VPN). In an embodiment, the secure connection may be communicated over the internet.

In an embodiment, the medical provider 130 may be a system that provides medical services to a patient by, for example, maintaining a patient's medical records. In an embodiment, the medical provider 130 may include a front end web service 132, private patient data 134, and a patient management system 136. The front end web service 132 may include a secure firewall that is used to keep the medical provider 130 secure and to protect against threats from the public internet. In some embodiments, the front end web service 132 may present the GUI that interfaces with the provider API 124 of CDC 120. The private patient data 134 may include a patient's medical records which must be kept private. The patient management system 136 may be a database that stores and manages the patient's medical records.

In embodiments of the disclosure, communications between the BGM 102 and the CDC 120 are enabled by formatting the messages into an SMS-compliant protocol. Following below are example SMS message formats that may be utilized in such communications between BGM 102 and CDC 120. One skilled in the art will appreciate that the below examples are not intended to be limiting to embodiments of the invention, and that other message formats may be utilized to achieve various embodiments of the invention.

In an embodiment, an SMS message that may be transmitted from the BGM 102 to the CDC 120 may be formatted as follows:

1. Single day: "NNNNNNNNNNYYMMDDHHMMSSCBBB . . . HHMMSSCBBB"

2. Consecutive days: "NNNNNNNNNNYYMMDDHHMMSSCBBB . . . HHMMSSCBBB+HHMMSSCBBB . . . HHMMSSCBB B"

3. Multiple days, no test results on one day: "NNNNNNNNNNYYMMDDHHMMSSCBBB . . . HHMMSSCBBB++HHMMSSCBBB . . . HHMMSSCBB B"

4. Empty (null) test record: "NNNNNNNNNNYYMDD"

5. Multiple SMS messages: "NNNNNNNNNNYYMMD-DHHMMSSCBBB . . . HHMMSSCBBB+HHMMSSCBBB . . . HHMMSSCBB B" and/or "NNNNNNNNNNYYM-MDDHHMMSSCBBB . . . HHMMSSCBBB+HHMMSS-CBBB . . . HHMMSSCBB B"

where,
"NNNNNNNNNN"=BGM phone number
"YYMMDD"=Date
"HHMMSS"=Time
"C"=Code (B/A/N—before meal/after meal/none).
"BBB"=Blood sugar.
"+"=Increment date by 1 day.

In general, SMS messages are limited to 160 characters. If it is assumed that four blood tests are performed by a user of the BGM 102 per day, a single SMS message may contain slightly more than 3 days of records.

In another embodiment, the CDC 120 to BGM 102 bidirectional SMS messages may be formatted as follows:

CDC 120 to BGM 102: "NNNNNNNNNNYYMMDDM"
where,
"NNNNNNNNNN"=CDC 120 phone number
"YYMMDD"=Date
"M"=Message code (0 . . . 9, A . . . Z).

In an embodiment, the message code, "M", may represent a sentence fragment that may be stored on the BGM 102 and used for an audio or visual presentation of the SMS message received by the BGM 102. In some embodiments, the medical provider 120 may interact with provider API 124 to indicate the particular message, and therefore message fragments, that are to be sent to a BGM 102 for presentation by the BGM 102 to a user of the BGM 102 or to the BGM itself.

BGM 102 to CDC 120: "NNNNNNNNNNYYMMD-DMAYYMMDDMA . . . YYMMDDMA"
where,
"NNNNNNNNNN"=BGM 102 phone number
"YYMMDD"=Date message was received
"M"=Message code (0 . . . 9, A . . . Z).
"A"=Patient answer (1/0). (In an embodiment, the patient or user may respond to a question by positioning a key on the BGM 102 that corresponds to a Yes or No answer.)

Similar to the above described message format for transmission of record information, an SMS message from the BGM 102 to the CDC 120 may contain multiple message and answer pairs in a single SMS message.

Figure 2:
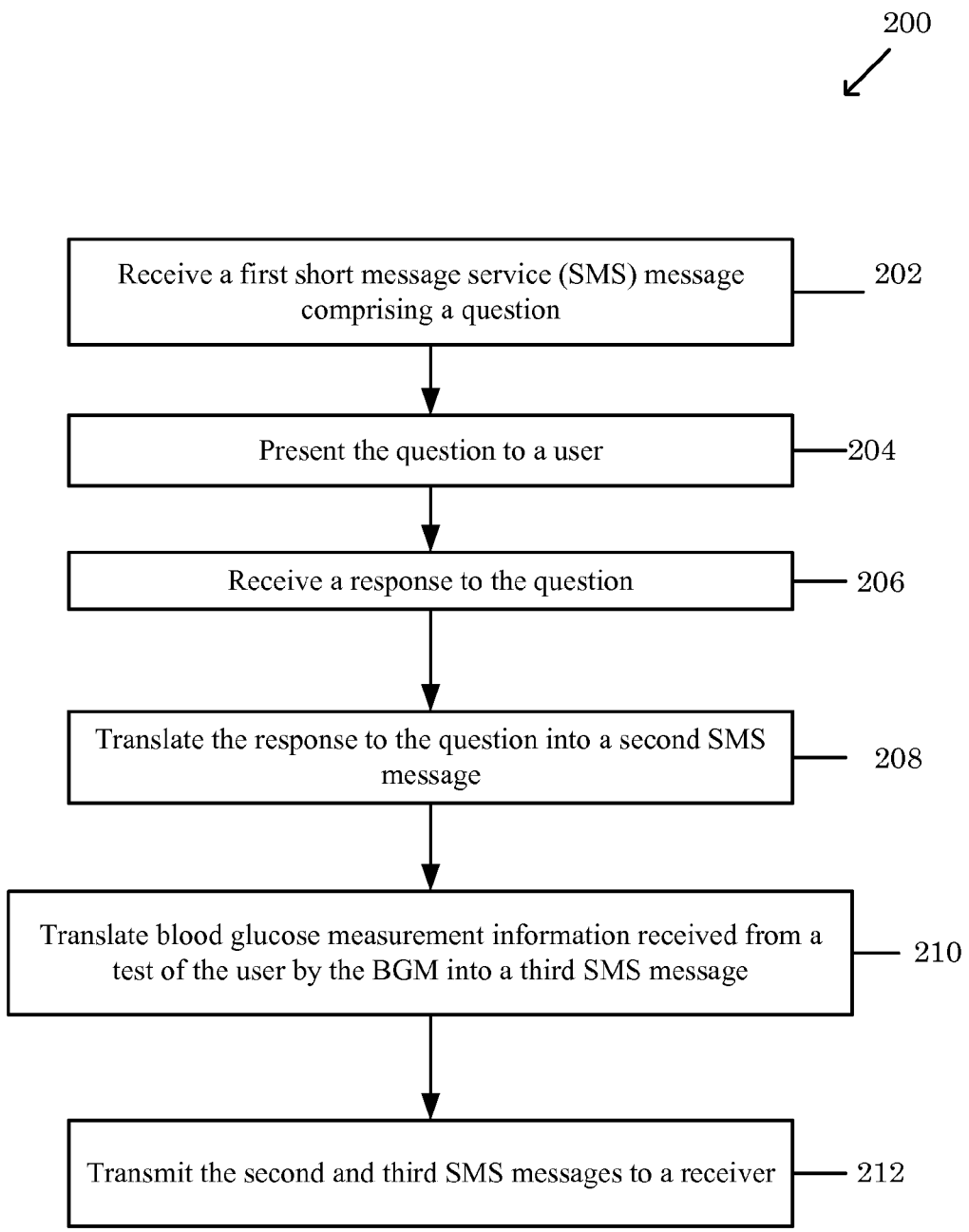
FIG. 2 is a flow diagram of a method for two way SMS enabled BGM and related communications in accordance with embodiments of the present invention.

FIG. 2 illustrates a method 200 performed by a BGM for two-way SMS-enabled communications to and from the BGM. Method 200 may be performed by processing logic that may comprise hardware (e.g., circuitry, dedicated logic, programmable logic, microcode, etc.), software (such as instructions run on a processing device), firmware, or a combination thereof. In one embodiment, method 200 is performed by BGM 102 of FIG. 1.

Method 200 begins at block 202, where the BGM 102 receives a first SMS message from the CDC 120 via the SMS gateway 112 and network 110. The first SMS message may include, but is not limited to, a question from the medical provider 130, and may be related to one or more of the following topics: 1) operations, administration, management, and provisioning (OAMP) functions of the BGM; 2) request to send a control solution; 3) a medical question or a reminder; or 4) an announcement. One skilled in the art will appreciate that other topics than those listed above may also be the subject of SMS messages in embodiments of the invention.

The OAMP functions of the BGM may include SMS messages that are intended to ask the patient to perform a specific task so that the BGM may operate as intended. Such questions may include, but are not limited to, a request to download new software, to synchronize the time clock of the BGM, or to reset the BGM.

In one embodiment, a request to send a control solution may be utilized to check that the BGM is calibrated correctly. A control solution is a standard liquid medium in which the contents are known. When the test of the control solution is received by the medical provider 130, the expected results of the control solution are compared against the received results of the test of the control solution to verify the accuracy of the BGM.

In some embodiments, a medical question or a reminder may be, for example, "are you testing your blood glucose levels three times per day as prescribed by the doctor?" An announcement may be, for example, "please test your blood glucose level 15 minutes after your evening meal." In one embodiment, an announcement is considered to be a question in which no answer is required.

At block 204 the BGM 102 presents the received question to a user of the BGM. In one embodiment, the question in the SMS message may be displayed on a visible screen display that is integrated with the BGM 102. In another embodiment, the question in the SMS message may be translated into a digital audio broadcasting format. The BGM 102 may be configured to audibly broadcast the question by storing fragments or snippets of voice samples and by retrieving and arranging the snippets in accordance with the question.

At block 206, the BGM 102 receives a response to the question from the user and/or from processing logic of the BGM device. In one embodiment, the BGM 102 may be configured with a keypad for the user to enter the response to the question. In another embodiment, the BGM 102 may be configured with a voice recognition module so that the user can verbally respond to the question. In an embodiment, if the question asked the user to send a control solution test, the response to the question may be a message from the BGM indicating the control solution test results. In a further embodiment, if the question involved OAMP, the response to the question may be a message from the BGM indicating an error code reading or a message indicating that there is no error.

Subsequently, at block 208 the BGM 102 translates the response to the question into a second SMS message and may direct the second SMS message to an outgoing message queue 106 of the BGM. In an embodiment, the message processor at the BGM receives data from the response to the question and translates the response by placing it in SMS-compliant format using a pre-determined SMS message format protocol, such as the example format discussed above, agreed to between the BGM and CDC. The second SMS message may then be transmitted from the outgoing message queue Then, at block 210 the BGM 102 translates blood glucose measurement information received from a test of the user into a third SMS message. In an embodiment, the BGM may direct the third SMS message to the outgoing message queue 106 to be transmitted at a certain time in the future. In an embodiment, the third SMS message may comprise information about a date, time, and a measured blood glucose level measured by the BGM. In another embodiment, the BGM may determine if the third SMS message is sent immediately or on a timed interval.

Lastly, at block 212, the BGM 102 transmits the second and third SMS messages to the CDC 120 via the SMS gateway 112 and the network 110. One skilled in the art will appreciate that the particular order in which the second and third SMS messages are sent may vary in implementations of embodiments of the invention. For example, the third SMS message may be sent prior to the second SMS message and vice versa. One skilled in the art will further appreciate that the second and third SMS messages may be related to each other in some embodiments, and, in other embodiments, may refer to discrete events that are unrelated to one another.

Figure 3:
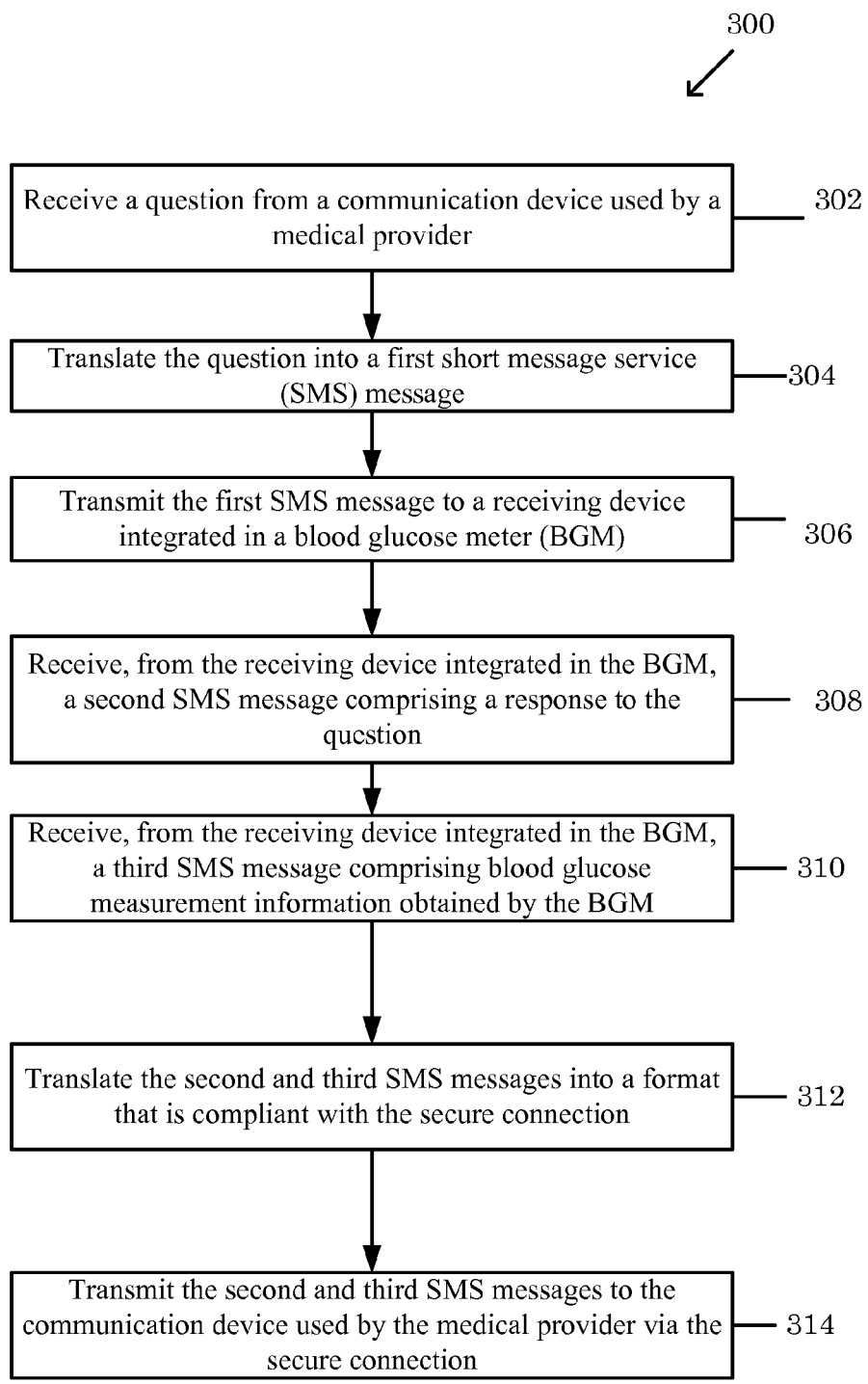
FIG. 3 is a flow diagram of another method for two way SMS enabled BGM and related communications in accordance with embodiments of the present invention.

FIG. 3 illustrates a method 300 performed by a CDC for communications with a two-way SMS-enabled BGM. Method 300 may be performed by processing logic that may comprise hardware (e.g., circuitry, dedicated logic, programmable logic, microcode, etc.), software (such as instructions run on a processing device), firmware, or a combination thereof. In one embodiment, method 300 is performed by CDC 120 of FIG. 1.

Method 300 begins at block 302, where the CDC receives a question from a medical provider via a secure connection. As discussed above, the question may be related to one or more of the following topics: 1) operations, administration, management, and provisioning (OAMP) functions of the BGM 102; 2) request to send a control solution; 3) a medical question or a reminder; or 4) an announcement. In one embodiment, the question is sent from a computer system operated by the medical provider.

In an embodiment, the CDC may receive, from the medical provider, information that pertains to a class of BGMs. A class of BGMs may be a group of BGMs in which the users of such BGMs are similarly situated. For example, if the medical provider aims to send a certain question to a predefined group of patients, then those BGMs that are associated with these patients are collectively considered to be a class. In an embodiment, the medical provider 130 may define a group of patients that are similarly situated and assign these patients to a class. The information related to the class of patients may be transmitted to the CDC. The CDC may associate the class of patients with their respective BGMs, thereby defining the class of BGMs.

At block 304, the CDC translates the question into a first SMS message by placing the question in SMS-compliant format using an SMS message format protocol as discussed above and agreed to between the BGM and CDC. Then, at block 306, the CDC transmits the first SMS message to a receiving device integrated in the BGM. In one embodiment, the first SMS message may be transmitted via a SMS gateway and/or a network.

In block 308, the CDC receives from the BGM a second SMS message comprising a response to the question. In one embodiment, the second SMS message is received via the SMS gateway and the network. In block 310, the CDC receives from the BGM a third SMS message comprising the user's blood glucose measurement information. In one embodiment, the third SMS message is received via the SMS gateway and the network.

In block 312, the CDC translates the second and third SMS messages into a format that is compliant with the secure connection and the front end web service of the medical provider by placing the SMS messages in a format using a secure connection format protocol as agreed to between the CDC and the medical provider. In block 314, the CDC transmits the second and third SMS messages to the medical provider via the secure connection. In some embodiments, the CDC may begin translating and transmitting the second SMS message before third SMS message is received, and vice versa.

Figure 4:
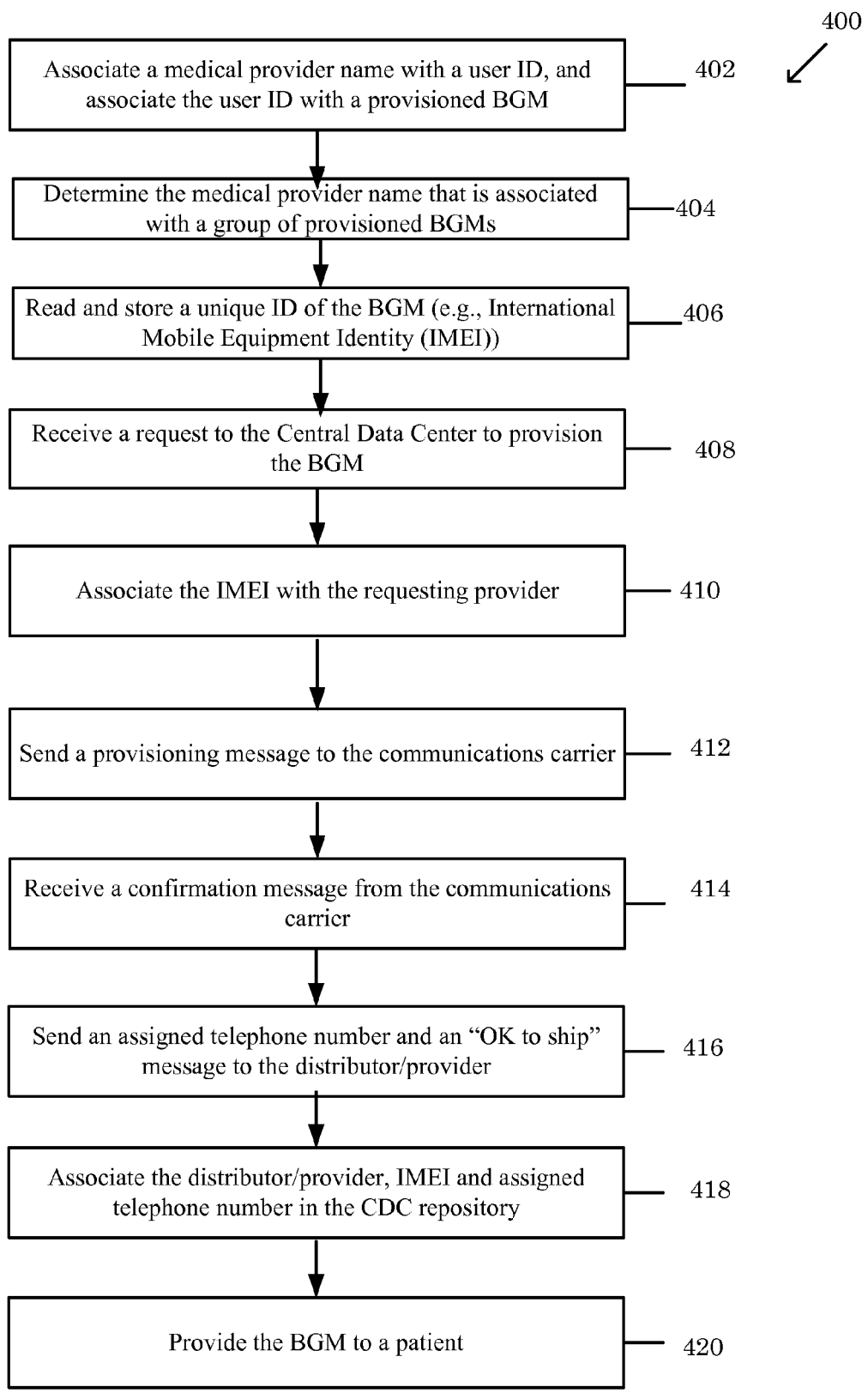
FIG. 4 is a flow diagram of a method for provisioning two way SMS enabled BGM and related communications in accordance with embodiments of the present invention.

FIG. 4 illustrates a method 400 for provisioning, for a medical provider, a two-way SMS-enabled BGM for use by a user/patient. Method 400 may be performed by processing logic that may comprise hardware (e.g., circuitry, dedicated logic, programmable logic, microcode, etc.), software (such as instructions run on a processing device), firmware, or a combination thereof. In one embodiment, method 400 is performed by CDC 120 of FIG. 1.

Method 400 begins at block 402, where the CDC associates a medical provider name (e.g., medical provider 130, as shown in FIG. 1) with an ID, and associates the ID with a provisioned BGM (e.g., BGM 102, as shown in FIG. 1). At block 404, the CDC determines the medical provider name that is associated with a group of provisioned BGMs. In block 406, the CDC reads and stores a unique ID of the BGM (e.g., International Mobile Equipment Identity (IMEI)). At block 408, the CDC receives a request to provision the BGM. At block 410, the CDC associates the IMEI of the BGM with the requesting provider. In one embodiment, the identification of the requesting medical provider (e.g., the determined medical provider name) is associated with the IMEI of the BGM at a database of the CDC.

Then, at block 412, the CDC sends a provisioning message to a communications carrier. In one embodiment, the communication carrier provides SMS communication capabilities for the BGM. At block 414, the CDC receives a confirmation message from the communications carrier. In one embodiment, the confirmation message may include a telephone number to assign to the BGM, where the telephone number acts as the identifying contact information for the BGM for purposes of SMS communications.

Subsequently, at block 416, the CDC sends the assigned telephone number received from the communication carrier and an "OK to ship" message to the medical provider. At block 418, the CDC associates the medical provider, IMEI and assigned telephone number together in a database maintained at the CDC. Lastly, at block 418, the BGM is provided to the patient and/or user. For example, the BGM may be shipped to the patient and/or user.

Figure 5:
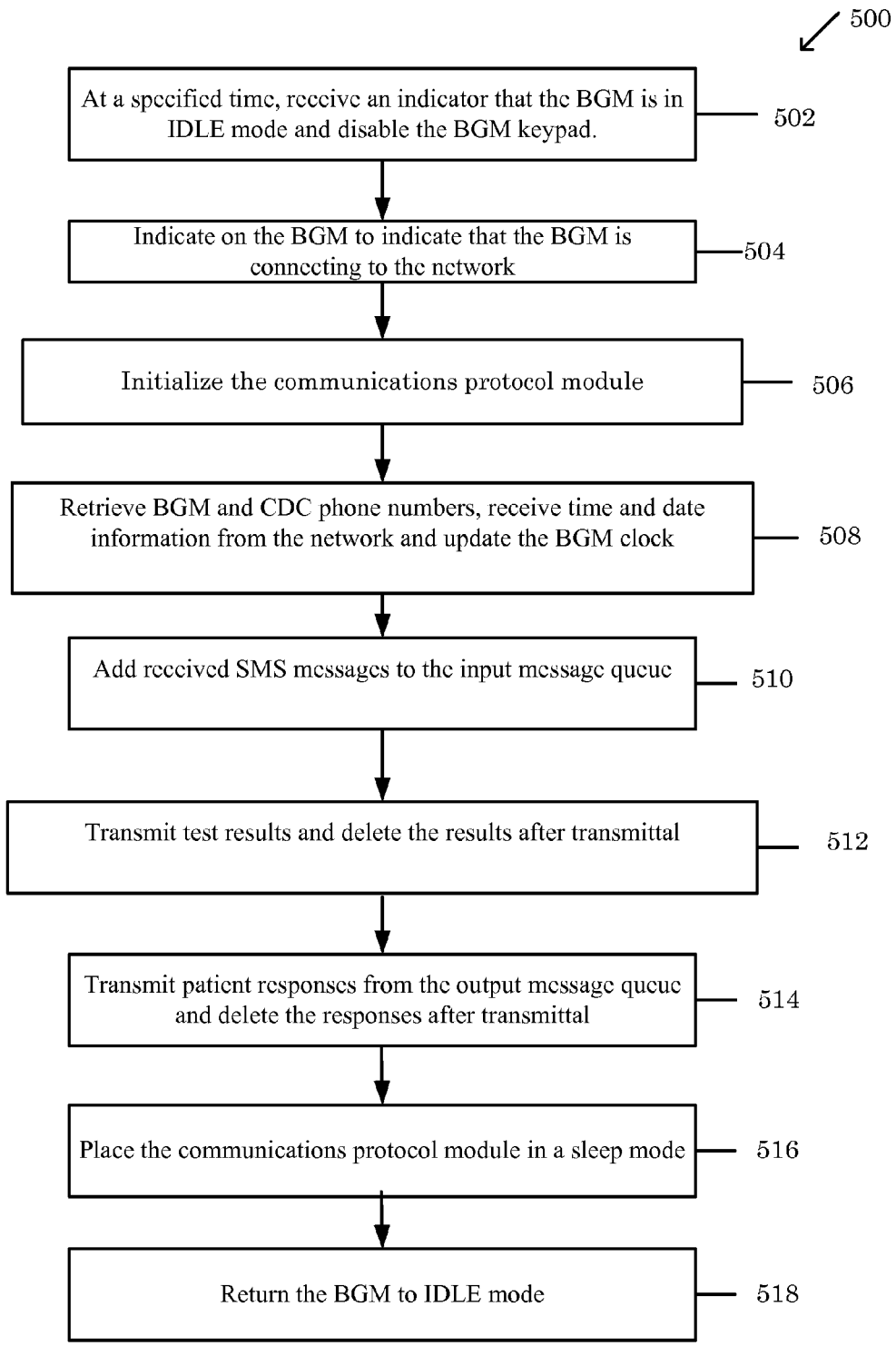
FIG. 5 is a flow diagram of a method for two way SMS enabled BGM and related communications in accordance with embodiments of the present invention.

FIG. 5 illustrates a method 500 for synchronization of a two-way SMS-enabled BGM and related communications. Method 500 may be performed by processing logic that may comprise hardware (e.g., circuitry, dedicated logic, programmable logic, microcode, etc.), software (such as instructions run on a processing device), firmware, or a combination thereof. In one embodiment, method 500 is performed by BGM 102 of FIG. 1.

Method 500 begins at block 502, where a BGM, at a specified time, (e.g., 1 AM) checks and receives an indication that the BGM is in IDLE mode. Upon receiving/confirming the IDLE mode indication, the BGM disables the keypad and/or other input device of the BGM. In block 504, the BGM displays a message (e.g., "C") on the BGM screen display to indicate that the BGM is connecting to a network.

Then at block 506, the BGM initializes a communications protocol module (e.g., the CDMA or GSM module as discussed above) of the BGM. At block 508, the BGM retrieves phone numbers for the BGM and for the CDC, receives time and date information from the network, and updates the BGM clock. Then, at block 510, the BGM adds any received SMS messages to an input message queue of the BGM.

Subsequently, at block 512, the BGM transmits other SMS messages that include blood glucose measurement test results. In some embodiments, the BGM may delete the test results after transmittal of the associated SMS messages. At block 514, the BGM may then transmit additional SMS message that include responses from at least one of a user of the BGM or the BGM itself. In one embodiment, these additional SMS messages are transmitted from an output message queue. The BGM may delete the responses associated with the additional SMS messages after their transmittal. At block

516, the BGM places the communications protocol module of the BGM in a sleep mode. Lastly, at block 518, the BGM returns to an IDLE mode state.

Figure 6:
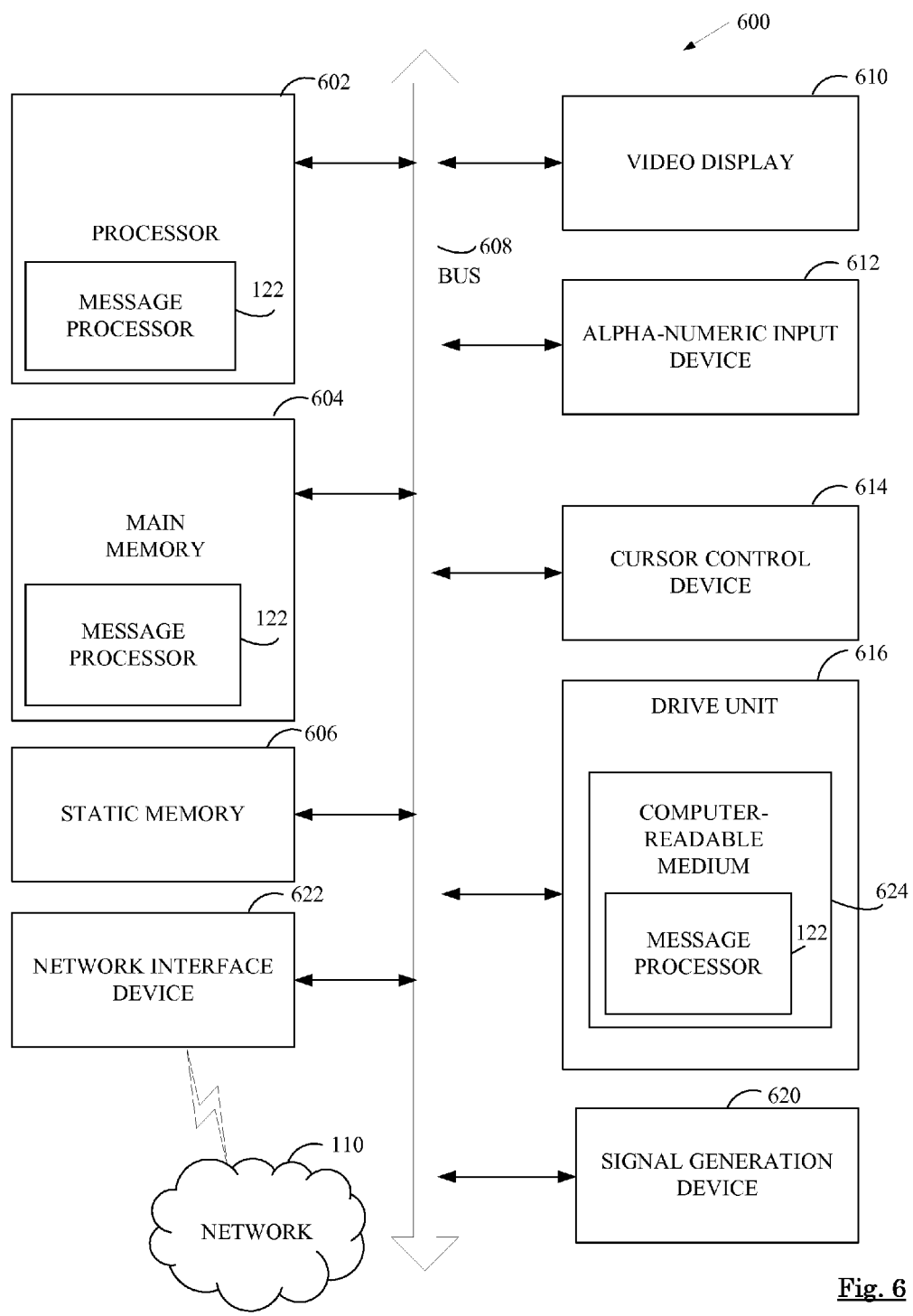
FIG. 6 is a block diagram of a computer system that may perform one or more of the operations described herein.

FIG. 6 illustrates a diagrammatic representation of a machine in the example form of a computer system 600 within which a set of instructions, for causing the machine to perform any one or more of the methodologies discussed herein, may be executed. In alternative embodiments, the machine may be connected (e.g., networked) to other machines in a LAN, an intranet, an extranet, or the Internet. The machine may operate in the capacity of a server or a client machine in a client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The computer system 600 includes a processing device (processor) 602, a main memory 604 (e.g., read-only memory (ROM), flash memory, dynamic random access memory (DRAM) such as synchronous DRAM (SDRAM) or Rambus DRAM (RDRAM), etc.), a static memory 606 (e.g., flash memory, static random access memory (SRAM), etc.), and a data storage device 616, which communicate with each other via a bus 608.

Processor 602 represents one or more general-purpose processing devices such as a microprocessor, central processing unit, or the like. More particularly, the processor 602 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processor 602 may also be one or more special-purpose processing devices such as an application specific integrated circuit (ASIC), a field programmable gate array (FPGA), a digital signal processor (DSP), network processor, or the like. The processor 602 is configured to execute instructions for performing the operations and steps discussed herein, illustrated in FIG. 6 by depicting instructions for message processor 122 within processor 602.

The computer system 600 may further include a network interface device 622. The computer system 600 also may include a video display unit 610 (e.g., a liquid crystal display (LCD) or a cathode ray tube (CRT)), an alphanumeric input device 612 (e.g., a keyboard), a cursor control device 614 (e.g., a mouse), and a signal generation device 620 (e.g., a speaker).

The data storage device 616 may include a computer-readable storage medium 624 on which is stored one or more sets of instructions (e.g., message processor 122) embodying any one or more of the methodologies or functions described herein. The message processor 122 may also reside, completely or at least partially, within the main memory 604 and/or within the processor 602 during execution thereof by the computer system 600, the main memory 604 and the processor 602 also constituting computer-readable storage media. The instructions for message processor 122 may further be transmitted or received over a network 110 via the network interface device 622.

While the computer-readable storage medium 624 is shown in an embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

Some portions of the detailed description have been presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "transmitting", "receiving", "translating", "extracting", "determining", and "broadcasting", "presenting", or the like, refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices.

The present disclosure also relates to an apparatus for performing the operations herein. This apparatus may be specially constructed for the required purposes, or it may include a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions.

Reference throughout this specification to "one embodiment" or "an embodiment" means that a particular feature, structure, or characteristic described in connection with the embodiment is included in at least one embodiment. Thus, the appearances of the phrase "in one embodiment" or "in an embodiment" in various places throughout this specification are not necessarily all referring to the same embodiment. In addition, the term "or" is intended to mean an inclusive "or" rather than an exclusive "or."

As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

It is to be understood that the above description is intended to be illustrative, and not restrictive. Many other embodiments will be apparent to those of skill in the art upon reading and understanding the above description. The scope of the disclosure should, therefore, be determined with reference to the appended claims, along with the full scope of equivalents to which such claims are entitled.

What is claimed is:

1. A method comprising:
   receiving, by a processing device integrated with a blood glucose meter (BGM), a first short message service (SMS) message comprising a question;
   presenting the question at the BGM;
   receiving a response to the question;
   translating the response to the question into a second SMS message;
   translating blood glucose measurement information and control solution measurement information into a third SMS message, the blood glucose measurement information comprising a first measurement received from a test of a blood sample of a user by the BGM, and the control solution measurement information comprising a second measurement received from a test of a non-blood standard liquid medium solution by the BGM for calibration of blood glucose measurement accuracy of the BGM; and
   transmitting the second and third SMS messages to a receiver.

2. The method of claim 1, wherein the third SMS message comprises information about a date of the test, a time of the test, and a measured blood glucose level measured by the test at the BGM.

3. The method of claim 1, wherein the question comprises at least one of a confirmation of personal information about the user, a request to change a frequency of the test of the user by the BGM, a request to perform an operation at the BGM, administration of the BGM, maintenance of the BGM, provisioning function of the BGM, or a request for the BGM to transmit the control solution measurement information.

4. The method of claim 1 further comprising:
   displaying the question on a visible screen integrated with the BGM.

5. The method of claim 1, wherein the third SMS message further comprises an error message.

6. The method of claim 1 further comprising:
   translating the first SMS message into a digital audio broadcasting format.

7. A method comprising:
   receiving, by a processing device, a question from a communication device of a medical provider, the question received via a secure connection between the processing device and the communication device of the medical provider;
   translating the question into a first short message service (SMS) message;
   transmitting the first SMS message to a receiving device integrated in a blood glucose meter (BGM);
   receiving, from a transmitting device integrated in the BGM, a second SMS message comprising a response to the question;
   receiving, from the transmitting device integrated in the BGM, a third SMS message comprising:
      blood glucose measurement information comprising a first measurement received from a test of a blood sample of a user by the BGM; and
      control solution measurement information comprising a second measurement received from a test of a non-blood standard liquid medium solution by the BGM for calibration of blood glucose measurement accuracy of the BGM;
   translating the second and third SMS messages into a format that is compliant with the secure connection; and
   transmitting, via the secure connection, the second and third SMS messages to the communication device of the medical provider.

8. The method of claim 7, wherein the third SMS message comprises information about a date of the test, a time of the test, and a measured blood glucose level measured by the test at the BGM.

9. The method of claim 7, wherein the question comprises at least one of a confirmation of information about the user, a request to change a frequency of the test of the user by the BGM, a request to perform an operation at the BGM, administration of the BGM, maintenance of the BGM, provisioning function of the BGM, or a request for the BGM to transmit the control solution measurement information.

10. The method of claim 7, further comprising:
    receiving, by the processing device via the secure connection, BGM class information from the communication device of the medical provider, the BGM class information comprising a group of BGMs associated with a group of patients.

11. A system comprising:
    a memory;
    a processing device communicably coupled to the memory; and
    a blood glucose data management program (BGDMP) executable from the memory by the processing device, the BGDMP configured to:
       receive a first short message service (SMS) message comprising a question;
       present the question;
       receive a response to the question;
       translate the response to the question into a second SMS message;
       translate blood glucose measurement information and control solution measurement information into a third SMS message, the blood glucose measurement information comprising a first measurement received from a test of a blood sample of a user by a blood glucose meter (BGM), and the control solution measurement information comprising a second measurement received from a test of a non-blood standard liquid medium solution by the BGM for calibration of blood glucose measurement accuracy of the BGM; and
       transmit the second and third SMS messages to a receiver.

12. The system of claim 11, wherein the third SMS message comprises information about a date of the test, a time of the test, and a measured blood glucose level measured by the test at the BGM.

13. The system of claim 11, wherein the question comprises at least one of a confirmation of information about the user, a request to change a frequency of the test of the user by the BGM, a request to perform an operation at the BGM, administration of the BGM, maintenance of the BGM, provisioning function of the BGM, or a request for the BGM to transmit the control solution measurement information.

14. The system of claim 11 further comprising:
display the question on a visible screen integrated with the BGM.

15. The system of claim 11, wherein the third SMS message further comprises an error message.

16. The system of claim 11 further comprising:
translate the first SMS message into a digital audio broadcasting format.

17. A non-transitory computer readable storage medium comprising data that, when executed by a processing device, causes the processing device to:
receive, by a processing device, a question from a communication device of a medical provider, the question received via a secure connection between the processing device and the communication device of the medical provider;
translate the question into a first short message service (SMS) message;
transmit the first SMS message to a receiving device integrated in a blood glucose meter (BGM);
receive, from a transmitting device integrated in the BGM, a second SMS message comprising a response to the question;
receive, from the transmitting device integrated in the BGM, a third SMS message comprising:
blood glucose measurement information comprising a first measurement received from a test of a blood sample of a user by the BGM; and
control solution measurement information comprising a second measurement received from a test of a non-blood standard liquid medium solution by the BGM for calibration of blood glucose measurement accuracy of the BGM;
translate the second and third SMS messages into a format that is compliant with the secure connection; and
transmit, via the secure connection, the second and third SMS messages to the communication device of the medical provider.

18. The non-transitory computer readable storage medium of claim 17, wherein the third SMS message comprises information about a date of the test, a time of the test, and a measured blood glucose level measured by the test at the BGM.

19. The non-transitory computer readable storage medium of claim 18, wherein the question comprises at least one of a confirmation of information about the user, a request to change a frequency of the test of the user by the BGM, a request to perform an operation at the BGM, administration of the BGM, maintenance of the BGM, provisioning function of the BGM, or a request for the BGM to transmit the control solution measurement information.

20. The non-transitory computer readable storage medium of claim 18, further to:
receive, by the processing device via the secure connection, BGM class information from the communication device of the medical provider, the BGM class information comprising a group of BGMs associated with a group of patients.

* * * * *